United States Patent [19]

Cesca et al.

[11] 4,113,790

[45] Sep. 12, 1978

[54] PROCESS FOR THE PREPARATION OF LINEAR ALPHA-OLEFIN OLIGOMERS, SUBSEQUENT HYDROGENATION THEREOF AND SATURATED PRODUCTS THUS OBTAINED

[75] Inventors: Sebastiano Cesca; Aldo Priola; Giuseppe Ferraris, all of San Donato Milanese (Milan), Italy

[73] Assignee: Snam Progetti, S.p.A., San Donato Milanese (Milan), Italy

[21] Appl. No.: 795,225

[22] Filed: May 9, 1977

Related U.S. Application Data

[63] Continuation of Ser. No. 601,183, Aug. 1, 1975, abandoned.

[51] Int. Cl.² ............................................. C07C 3/10
[52] U.S. Cl. ........................ 260/683.15 B; 260/683.9
[58] Field of Search .................... 260/683.15 B, 683.9

[56] References Cited

U.S. PATENT DOCUMENTS

| | | | |
|---|---|---|---|
| 2,360,699 | 10/1944 | McAllister et al. | 260/683.15 B |
| 2,540,580 | 2/1951 | Heinrich | 260/683.15 B |
| 2,970,133 | 1/1961 | Sistrunk | 260/683.15 B |
| 3,842,134 | 10/1974 | Pratt | 260/683.15 B |
| 3,907,924 | 9/1975 | Isa et al. | 260/683.15 B |

*Primary Examiner*—C. Davis
*Attorney, Agent, or Firm*—Morgan, Finnegan, Pine, Foley & Lee

[57] ABSTRACT

This invention relates to the preparation of linear alpha-olefin oligomers and more particularly to the catalyst system which consists of a two component mixture comprising an aluminium halide and a compound capable of reacting with said aluminium halide and selected among
 (a) halogens or interhalogenic compounds,
 (b) halogenated compounds having the formula

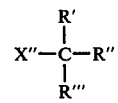

in which R', R", R''', represent H or alkyl or aryl
 (c) metal halides By the above catalyst system oligomers can be prepared with high yields and with an easier control and performance of the reaction, starting from linear alpha-olefins having 3 to 12 carbon atoms.

6 Claims, No Drawings

PROCESS FOR THE PREPARATION OF LINEAR ALPHA-OLEFIN OLIGOMERS, SUBSEQUENT HYDROGENATION THEREOF AND SATURATED PRODUCTS THUS OBTAINED

This is a continuation, of application Ser. No. 601,183 filed Aug. 1, 1975 and now abandoned.

The present invention relates to a process for the preparation of oligomers starting from linear alpha-olefins, to the subsequent hydrogenation thereof as well as to the saturated oligomer products thus obtained.

It is known that the paraffinic oils have found, in the last years, a broad application coverage in the feeding and pharmaceutical industry, in agriculture, as diluents of antiparasitic agents, rubber extenders, plastifiers, lubricating oils.

They are usually obtained by refining suitable fractions of the crude product; however the recent situation of a poor crude product disposal and the high cost increase have promoted many difficulties in the production of the paraffinic oils.

An alternative way for obtaining said oils is constituted by the cationic oligomerization of linear alpha-olefins, having above all from 3 to 6 carbon atoms, that give rise to low molecular weight oily products containing residual unsaturations in the chain, which may be lowered through a hydrogenation process producing a saturated product.

However, the known methods, substantially based on the employment of Friedel-Crafts halides, have some remarkable drawbacks, such as the low reaction yields, difficulties in controlling the reaction conditions and, hence, a difficult realization thereof.

We have now found that a first object of the present invention, is a process for the preparation of linear alpha-olefin oligomers which make use of a particular catalyst system that, with respect to the one still now employed advantage of giving higher polymer yields, more easy performance and reaction control.

By means of the inventive catalyst system it is possible to prepare oligomers starting from linear alpha-olefins having a carbon atom number of from 3 to 12, particularly propylene, butene-1 and pentene-1 oligomers.

It is constituted by two components selected between the two following classes of compounds:

(a) an aluminum halide having the formula $AlX_3$ in which X is a halogen atom;

(b) a compound able to react with the halides of the preceding class to give the catalytic species which is the starter of the polymerization, such compound being selected from the ones belonging to:
  (I) halogens or interhalogenic compounds having the general formula X'Y in which X' and Y, the same or different are selected among chlorine, bromine, iodine and fluorine,
  (II) compounds having the general formula

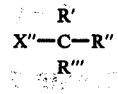

in which X" is halogen, R' R" R'" are hydrogen atoms or alkyl or aryl radicals, the same or different, having 1 to 12 carbon atoms, with the proviso they are not all contemporaneously hydrogen, (III) metal halides having the general formula

in which X'" is a halogen, Y' is oxygen or sulphur, Me is a metal selected among Sn Si B Ti Pb Sb As Bi Mg V, m is a whole number that may be zero too, n is a whole number and the 2m + n sum is equal to the metal valence.

Examples of employable aluminium halides are $AlCl_3$ $AlBr_3$ and $AlI_3$ while compounds belonging to the class (b) are $Cl_2$ $Br_2$ $I_2$ $F_2$ ICl IBr as to the first sub-class, tertbutyl-chloride, isopropylchloride, benzylchloride, isopropylbromide, tert-butylbromide as to the second sub-class and $SnCl_4$ $SiCl_4$ $BCl_3$ $TiCl_4$ $PbCl_4$ $SbCl_5$ $AsCl_5$ etc., as to the third sub-class.

The reaction is carried out in heterogeneous phase since aluminum halide is employed under the shape of a suspension finely subdivided in a medium generally selected from the hydrocarbons having a carbon atom number from 3 to 12, however the same may be carried out also without any solvent when the solvent is constituted by the excess of the monomer.

The two components of the catalyst system may be introduced into the reaction medium in the same moment or it is also possible to add the same separately and the addition order does not affect the obtainable catalytic species: the molar ratio between the component (a) and the component (b) may range from 0.1 to 5, preferably from 0.5 to 2.

The reaction is carried out at temperatures ranging from $-30°$ to $+80°$ C., preferably from $-10°$ to $+60°$ C.

The products, obtained from the polymerization have an average molecular weight varying from 200 to 3000; they contain residual unsaturations that can be expressed as bromine number (bromine grams absorbed from 100 grams of polymer) which is determined according to many methods, from which we draw the one ASTM D 1159.

The unsaturations present at the end of the oligomerization may be reduced or completely decreased through a hydrogenation reaction, constituting the second object of the present invention, which is carried out at temperatures of from 150° to 300° C., at partial hydrogen pressures of from 20 to 150 atmospheres in the presence of hydrogenation catalysts such as, for instance, nikel on Kieselghur, Ni-Raney, Pd on carbon, Pt on carbon. Possible residual traces of unsaturated products (bromine number of the product lower than 0.1) may be at last removed by passing the compounds on absorbing silicious earths to give the saturated product which constitute the third object of the present invention.

The aforesaid and the working formalities will be more clear by examining the following illustrative examples, which are not to be considered as a limitation to the invention.

EXAMPLE 1

35 g of butene-1 and 50 cm³ of n-pentane were introduced under pressure into a steel autoclave, having 300 cm³ capacity, equipped with a magnetic stirred and a thermometric sheath, previously dried under vacuum; the temperature was stabilized at + 14° C., and then, by a nitrogen overpressure, were contemporaneously and gradually added a suspension in n-pentane of $AlCl_3$ sublimated and grinded in a steel-ball mill, corresponding to 0.830 mmole, and 1.0 mmole of $Cl_2$ diluted in 10 $cm^3$ of n-pentane distilled and cooled at $-78°$ C.

The temperature increased up to $+26°$ C. and the reaction was carried out over 30'. Then the polymerization was stopped by a methyl-alcohol addition: the unreacted monomer was flashed and the resulting product was washed with water added with NaOH in order to remove the catalyst traces and, at last, washed with distilled water till neutrality.

The hydrocarbon phase was then distilled till a total elimination of the solvent: 21.35 g were obtained (yield = 61.0%) of dry polymer having an average osmometric molecular weight $M_n$ equal to 764, an unsaturation content, expressed as bromine number, equal to 28.8, determined according to the method ASTM D 1159, and a residual $Cl_2$ content equal to 552 ppm.

Contemporaneously and according to the same techniques, a a standard test was carried out by introducing into the autoclave the same amounts of solvent and monomer and, then, a suspension of $AlCl_3$ sublimited and grinded, in distilled n n-pentane, corresponding to 0.720 mmole: the temperature increased from $+17$ to $+24°$ C. and the reaction was prosecuted over 60'. The reaction was stopped by methyl alcohol, the unreacted monomer was flashed, the oligomer was washed and distilled: 11.05 g (yield = 31.7%) were obtained of dry polymer having an average osmometric molecular weight $M_n$ equal to 710, bromine number equal to 32.0 and a residual $Cl_2$ content equal to 258 ppm.

The product obtained from the reaction catalyzed by the catalyst system $AlCl_3 + Cl_2$ underwent a hydrogenation reaction in order to elminate the unsaturations present in the polymeric chain according to the following items: g 12.0 of polybutene-1 and 0.80 g of Ni-Raney, prepared according "A.I. Vogel - Practical Organic Chemistry - Longmans, Green and Co. Edit., pag. 870 (1956)" were introduced into an autoclave equipped with a mechanical stirrer and a thermometric sheath. The temperature was brought at 270° C. at a $H_2$ pressure of 90 atmospheres and the reaction prosecuted over 20 hours. Then the whole was cooled, the autoclave was depressurized and the hydrogenated product was analyzed as to the residual unsaturations which corresponded to a bromine number of 0.35.

EXAMPLE 2

According to the same formalities of example 1, the autoclave was fed with the same amounts of solvent and monomer, then the reaction was started at the temperature of $+25°$ C. by contemporaneously introducing a suspension of $AlCl_3$, sublimated and grinded, in distilled n-pentane corresponding to 0.826 mmole, and a solution containing 1.0 mmole of $Br_2$ diluted in 10 $cm^3$ of n-pentane distilled and cooled at $-78°$ C. The temperature increased up to $+30°$ C. and the reaction was prosecuted over 30'.

After stopping, g 20.48 of dry polymer (yield = 58.5%) were obtained having $\overline{M}_n = 822$ and a bromine number equal to 25.6.

The product was then hydrogenated according to example 1 by introducing g 12.0 of oligomer and 0.80 g of Ni-Raney prepared according to example 1: the temperature was brought to 270° C. and the pressure of $H_2$ to 90 atmospheres over 20 hours. The hydrogenated product was then analyzed as to the residual unsaturation, thus obtaining a bromine number of 0.48.

EXAMPLE 3

According to the same techniques of example 1, the autoclave was fed by the same amounts of solvent and monomer: the reaction was started at the temperature of $+14°$ C. by contemporaneously introducing a suspension of $AlCl_3$ sublimated and grinded in distilled n-pentane, corresponding to 0.845 mmole, and 0.9 mmole of $I_2$ suspended in 10 $cm^3$ of distilled n-pentane.

The temperature raised up to $+19°$ C. and the reaction was prosecuted over $17^h$ and 45'. 24.2 g of dry polymer (yield = 69.3%) were obtained, it having $\overline{M}_n = 882$ and bromine number of 23.2.

The product was then subjected to hydrogenation according to the formalities of example 1: a hydrogenated product was obtained having characteristics quite similar to the ones already described.

EXAMPLE 4

According to the same techniques of example 1, the same amounts of solvent and monomer were introduced: then the temperature was stabilized at $+15°$ C. and the polymerization was started by contemporaneously introducing a suspension of $AlCl_3$ sublimated and grinded, in distilled n-pentane corresponding to 0.797 mmole and a solution containing 1.0 mmole of ICl diluted in 10 $cm^3$ of distilled n-pentane. The temperature arose to $+28°$ C. and the reaction was prosecuted over 60'.

26.06 g of dry product were obtained (yield = 74.5%) having $\overline{M}_n = 780$, a bromine number equal to 24.2 and a residual $Cl_2$ content equal to 540 ppm.

EXAMPLE 5

According to the same technique of example 1, the same amounts of monomer and solvent were introduced: then the polymerization was started at the temperature of $+13°$ C. by contemporaneously introducing a suspension of $AlCl_3$ sublimated and finely grinded, in distilled n-pentane corresponding to 0.830 mmole, and a solution containing 1.0 mmole of IBr diluted in 10 $cm^3$ of distilled n-pentane.

The temperature increased up to $+37°$ C. and the reaction was prosecuted over 60'. After stopping, g 20.05 (yield = 57.3%) were obtained of dry product having $\overline{M}_n = 832$ a bromine number = 25.5.

EXAMPLE 6

Use was made of the same technical procedure as for example 1; accordingly the same amounts of solvent and monomers were introduced, then the reaction was started by contemporaneously introducing, at $+13°$ C., a suspension of Al $AlCl_3$, sublimated and grinded, in distilled n-pentane corresponding to 0.895 mmole and a solution containing 0.9 mmole of tert-butylchloride diluted in 10 $cm^3$ of n-pentane.

The temperature increased up to $+35°$ C. and the reaction was prosecuted over 30'. G 24.17 of dry product were obtained (yield = 76.7%) having $\overline{M}_n = 520$, bromine number equal to 20.9 and residual $Cl_2$ equal to 510 ppm.

EXAMPLE 7

According to the same techniques of example 1, the same amounts of solvent and monomer were introduced: then the reaction was started by contemporaneously adding, at $+14°$ C., a distilled n-pentane suspension of $AlCl_3$ sublimated and grinded, corresponding to 0.655 mmole and a solution containing 0.6 mmole of isopropylchloride diluted in 10 cm³ of distilled n-pentane.

The temperature increased till +30° C. and the reaction was prosecuted over 30'. After stopping, g 23.52 of dry oligomer were obtained (yield = 67.2%), having $\overline{M}_n$ = 455, bromine number equal to 23.9, and Cl₂ content lower than 100 ppm.

EXAMPLE 8

According to the same operative formalities of example 1, the autoclave was charged by the same amounts of solvent and monomer: then the polymerization was started by a contemporaneous addition, at +17° C., of a distilled n-pentane suspension of AlCl₃ sublimated and grinded, corresponding to 1.0 mmole and a solution containing 1.0 mmole of benzyl chloride diluted in 10 cm³ of distilled n-pentane.

The temperature increased up to +37° C. and the reaction prosecuted over 30'. G 24.61 of dry product were obtained (yield = 70.3%) having $\overline{M}_n$ = 419, bromine number = 51.6 and chlorine content equal to 880 ppm.

EXAMPLE 9

The same amounts of solvent and monomer were introduced into the autoclave according to the formalities of example 1, then the reaction was started by contemporaneously adding, at +20° C., a suspension of AlCl₃ sublimated and grinded, in distilled n-pentane, corresponding to 0.802 mmole and a solution of 0.4 mmole of SnCl₄ in 10 cm³ of distilled n-pentane.

The temperature arose to +40° C. and the reaction prosecuted over 135'. After stopping, g 19.0 of dry polymer (yield = 54.5%) were obtained, having $\overline{M}_n$ = 670, bromine number = 31.2 and a residual Cl₂ content equal to 350 ppm.

EXAMPLE 10

By following the same techniques of example 1, the autoclave was charged with the same amounts of solvent and monomer, and, then, the reaction was started at the temperature of +16° C. by contemporaneously adding a suspension of AlCl₃ sublimated and grinded, in distilled n-pentane, corresponding to 0.933 mmole and a solution containing 2.0 mmoles of BCl₃ diluted in 10 cm³ of n-pentane.

The temperature increased up to +42° C. and the reaction was prosecuted for 30'. After stopping, g 24.5 were obtained of dry polymer (yield = 70.0%) having $\overline{M}_n$ = 560, bromine number = 34.0 and a residual Cl₂ content = 420 ppm.

What we claim is:

1. Process for the preparation of a polymer having a molecular weight of from 200–3000 from a linear alpha-olefin having a carbon atom number of from 3 to 12 wherein the reaction is carried out in the presence of a catalyst system consisting of:
   (a) an aluminum halide having the formula AlX₃ in which X is a halogen atom, and
   (b) a compound able to react with the aforesaid halides to give the catalyst species capacity to start the polymerization selected from the ones belonging to one of the following classes:
      (I) halogen or interhalogen compounds having the general formula X'Y in which X' and Y, the same or different, and are selected from the group consisting of chlorine, bromine, iodine and fluorine; or
      (II) a metal halide having the formula BCl₃ said reaction being carried out in the presence of a suspension medium selected from the hydrocarbons having a carbon atom number of from 3 to 12.

2. Process as claimed in claim 1 wherein (b) is halogen or an interhalogen compound having the general formula X'Y in which X' and Y, the same or different, and are selected from the group consisting of chlorine, bromine, iodine and fluorine.

3. Process as claimed in claim 1 wherein (b) is BCl₃.

4. Process for the preparation of a polymer having a molecular weight of from 200–3000 from a linear alpha-olefin having a carbon atom number of from 3 to 12 wherein the reaction is carried out in the presence of a catalyst system consisting of:
   (a) an aluminum halide wherein X is a halogen atom,; and
   (b) compounds having the formula:

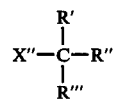

in which X" is halogen, R', R", R''' are members of the group consisting of hydrogen, alkyl and aryl radicals which may be the same or different, having from 1 to 12 carbon atoms with the proviso that not all are contemporaneously hydrogen.

5. Process as claimed in claim 4 wherein (b) is t-butylchloride.

6. Process as claimed in claim 4 wherein (b) is benzyl chloride.

UNITED STATES PATENT AND TRADEMARK OFFICE
CERTIFICATE OF CORRECTION

PATENT NO. : 4,113,790
DATED : September 12, 1978
INVENTOR(S) : Sebastiano Cesca, Aldo Priola and Giuseppe Ferraris It is certified that error appears in the above-identified patent and that said Letters Patent are hereby corrected as shown below:

On the cover page, after line [22] insert

--Foreign Application Priority Data

August 2, 1974    Italy.............25937 A/74--

Signed and Sealed this

Twenty-third Day of October 1979

[SEAL]

Attest:

RUTH C. MASON
Attesting Officer

LUTRELLE F. PARKER
Acting Commissioner of Patents and Trademarks